United States Patent [19]

Nedelec et al.

[11] Patent Number: 4,694,011
[45] Date of Patent: Sep. 15, 1987

[54] NOVEL 7-HYDROXY-INDOLES

[75] Inventors: Lucien Nedelec, Le Raincy; Gilles Hamon, Montrouge; Patrick Fauveau, Livry Gargan; Claude Oberlander, Paris, all of France

[73] Assignee: Roussel Uclaf, Paris, France

[21] Appl. No.: 838,242

[22] Filed: Mar. 10, 1986

[30] Foreign Application Priority Data

Mar. 12, 1985 [FR] France .................. 85 03585

[51] Int. Cl.$^4$ .................. C07D 209/34; A61K 31/40
[52] U.S. Cl. .................. 514/323; 546/201; 546/226; 546/232
[58] Field of Search .................. 546/201; 514/323

[56] References Cited

U.S. PATENT DOCUMENTS 4,332,808  6/1982  Guillaume et al. .................. 546/201
4,435,408  3/1984  Nedelec et al. .................. 546/201

FOREIGN PATENT DOCUMENTS 2458549  1/1981  France .

OTHER PUBLICATIONS

Hacksell et al. J. Med. Chem., 24, (1981), pp. 1475–1482.

Primary Examiner—Joseph Paul Brust
Attorney, Agent, or Firm—Bierman and Muserlian

[57] ABSTRACT

Novel 7-hydroxy-indoles of the formula

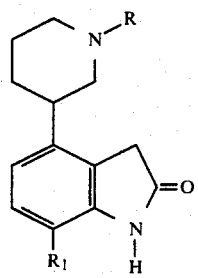

wherein R is selected from the group consisting of hydrogen, alkyl of 1 to 5 carbon atoms, cycloalkylalkyl of 4 to 7 carbon atoms and aralkyl of 7 to 12 carbon atoms optionally substituted by one or more members of the group consisting of alkyl and alkoxy of 1 to 5 carbon atoms, halogen and alkenyl and alkynyl of 3 to 5 carbon atoms with the multiple bond being other than between the carbons $\alpha$- and $\beta$- to the nitrogen atom, $R_1$ is selected from the group consisting of —OH, alkoxy of 1 to 5 carbon atoms, phenoxy and phenylalkoxy of 7 to 9 carbon atoms and their non-toxic, pharmaceutically acceptable acid addition salts having remarkable dopaminergic properties with few central effects and a novel process and novel intermediates for their preparation.

15 Claims, No Drawings

NOVEL 7-HYDROXY-INDOLES

STATE OF THE ART

French Patent No. 2,458,549 describes derivatives of 4-(piperidin-3-yl)-1H-indoles having marked dopaminergic stimulating properties at the central level. U.S. Pat. Nos. 4,435,408 and 4,332,808 and J. Med. Chem., Vol. 24 (1981), p. 1475–1482 describe related indoles.

OBJECTS OF THE INVENTION

It is an object of the invention to provide the novel indoles of formula I and their non-toxic, pharmaceutically acceptable acid addition salts and a novel process and novel intermediates for their preparation.

It is another object of the invention to provide novel compositions and method for the treatment of peripheric circulatory problems, cardiac insufficiencies, cerebral vascular accidents and arteriopathy.

These and other objects and advantages of the invention will become obvious from the following detailed description.

THE INVENTION

The novel compounds of the invention are selected from the group consisting of 7-hydroxy-indoles of the formula

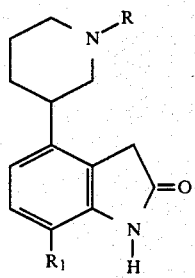

wherein R is selected from the group consisting of hydrogen, alkyl of 1 to 5 carbon atoms, cycloalkylalkyl of 4 to 7 carbon atoms and aralkyl of 7 to 12 carbon atoms optionally substituted by one or more members of the group consisting of alkyl and alkoxy of 1 to 5 carbon atoms, halogen and alkenyl and alkynyl of 3 to 5 carbon atoms with the multiple bond being other than between the carbons α- and β- to the nitrogen atom, $R_1$ is selected from the group consisting of —OH, alkoxy of 1 to 5 carbon atoms, phenoxy and phenylalkoxy of 7 to 9 carbon atoms and their non-toxic, pharmaceutically acceptable acid addition salts.

Examples of alkyl of 1 to 5 carbon atoms are methyl, ethyl, n-propyl and isopropyl and examples of cycloalkylalkyl of 4 to 7 carbon atoms are cyclopropylmethyl and cyclobutylmethyl. Examples of arylalkyl of 7 to 12 carbon atoms are benzyl, phenethyl and naphthylmethyl and the aryl may be plurisubstituted. Examples of alkoxy of 1 to 5 carbon atoms are methoxy, ethoxy, isopropoxy and n-propoxy and examples of halogen are chlorine and bromine. The alkenyl and alkynyl of 3 to 5 carbon atoms are preferably allyl or propargyl. Phenylalkoxy examples are benzyloxy and phenethoxy.

Examples of suitable acids for the formation of non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkanesulfonic acids such as methanesulfonic acid and ethanesulfonic acid, aryl sulfonic acids such as benzene sulfonic acid and p-toluene sulfonic acid and arylcarboxylic acids such as benzoic acid.

Among the preferred compounds of formula I are those wherein $R_1$ is hydroxy and those wherein R is hydrogen or alkyl of 1 to 5 carbon atoms and their acid addition salts. A preferred compound of formula I is 1,3-dihydro-7-hydroxy-4-(3-piperidinyl)-2H-indol-2-one and its non-toxic, pharmaceutically acceptable acid addition salts.

The novel process of the invention for the preparation of the compounds of formula I comprises reacting a compound of the formula

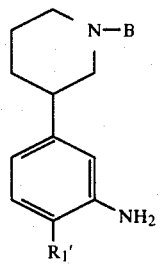

wherein $R_1'$ has the value of $R_1$ other than hydroxy and B is a reversible blocking agent of a secondary amine, activated in the form of a haloamine, with ethyl methylthioacetate in the presence of a base and then with an acid to obtain a compound of the formula

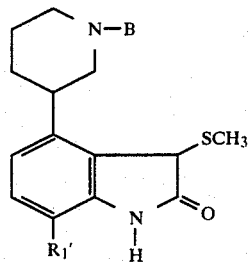

desulfurizing the latter to obtain a compound of the formula

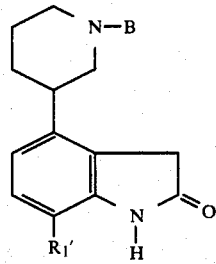

reacting the latter with a deblocking agent of a secondary amine to obtain a compound of the formula

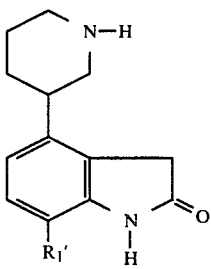

optionally isolating and salifying the latter or reacting the latter with a hydroxy deblocking agent to obtain a compound of the formula

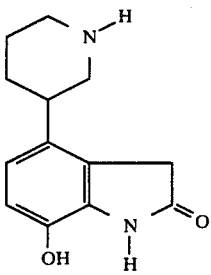

optionally isolating and salifying the latter or reacting the latter with an agent capable of introducing R' which is R other than hydrogen to obtain a compound of the formula

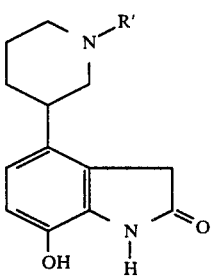

optionally isolating and salifying the latter or reacting the compound of formula $I_A$ with an agent capable of introducing R' to obtain a compound of the formula

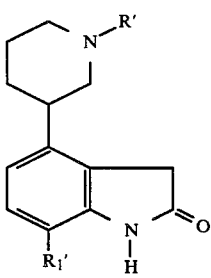

optionally isolating and salifying the latter or reacting the latter with a hydroxy deblocking agent to obtain a compound of formula $I_C$ which is isolated and optionally salified.

Examples of B blocking group are benzyl and trifluoroacetyl and the aromatic amine activation is preferably effected in the form of a chloramine such as with a hypchlorite like sodium hypochlorite or tert.-butyl hypochlorite. The reaction with ethyl methylthioacetate is effected in the presence of a base such as triethylamine or an alkali metal alcoholate such as sodium ethylate. The acid to effect cyclization is a mineral acid such as hydrochloric acid or hydrobromic acid or an organic acid. The desulfurization of the compound of formula III is preferably effected Raney nickel.

The method of deblocking the secondary amine may be one of those usually used for such deblocking such as catalytic hydrogenation in the case of benzyl or basic hydrolysis, for example, with a mineral base such as potassium hydroxide or sodium hydroxide or a carbonate such as sodium carbonate or potassium carbonate, or an acid such as hydrobromic acid or hydrochloric acid at reflux in the case of trifluoroacetyl.

The hydroxyl deblocking can be carried out hot, for example, with hydrobromic acid or pyridine hydrochloride at reflux and the salt can also be obtained directly. It can be effected cold, for example with boron tribromide whereby the product of formula $I_B$ or $I_C$ is obtained in the form of a base. It can also be effected by catalytic hydrogenation when the hydroxyl is blocked in the form of benzyl ether.

The agent capable of introducing R' is preferably a halide of the formula $$Hal-R'' \qquad XI$$

wherein R" has the significance of R already indicated other than hydrogen and methyl. The halide of formula XI can be a chloride or a bromide, but preferably is an iodide and it reacts advantageously with the secondary amines of formulae $I_A$ and $I_B$ in the presence of an acid binding agent such as an alkali metal carbonate like potassium carbonate in a solvent such as dimethylformamdie.

To introduce R' into the compounds of formulae $I_A$ and $I_B$, the operation can also be by reacting the compounds of formulae $I_A$ and $I_B$ with a derivative (according to the case aldehyde or a ketone) of the formula

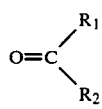

wherein $R_1$ and $R_2$ are such that

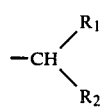

has the significance of R already indicated with the exception of hydrogen in the presence of a reducing agent such as alkali metal borohydride or cyanoborohydride such as sodium borohydride or cyanoborohydride, or catalytic hydrogenation. For example, if the derivative of formula XII is formaldehyde or acetaldehyde, the methyl and ethyl values are obtained respectively for R'.

In a variation of the process of the invention for the preparation of compounds of formula I, a compound of the formula

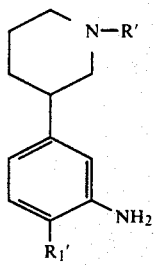

II' wherein R' is R other than hydrogen and R₁' is R₁ other than -OH activated in the form of a haloamine is reacted with ethyl methylthioacetate in the presence of a base and then with an acid to obtain a compound of the formula

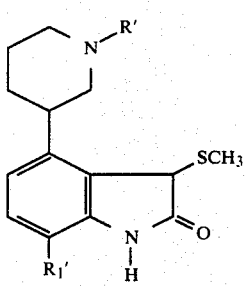

III' desulfurizing the latter to obtain a compound of formula $I_D$, optionally isolating and salifying the latter or reacting the latter with a hydroxyl deblocking agent to obtain the compound of formula $I_C$, optionally isolating and salifying the latter or when R' is benzyl, the compound of formula $I_C$ is reacted with a benzyl deblocking agent to obtain a compound of formula $I_B$ or when R' is benzyl, the compound of formula $I_D$ is reacted with a benzyl deblocking agent to form a compound of formula $I_A$ which is optionally isolated and salified or reacted with a hydroxyl deblocking agent to obtain a compound of formula $I_B$ which is isolated and optionally salified.

The starting compounds of formula II may be prepared by reacting a magnesium derivative of a compound of the formula

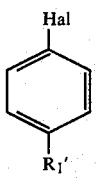

V when Hal is chlorine or bromine with a piperidone of the formula

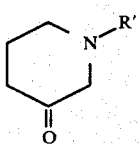

VI to obtain a compound of the formula

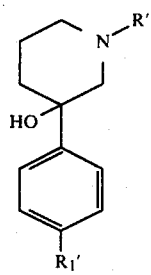

VII wherein R' and R₁' have the above definitions, dehydrating the latter to form a compound of the formula

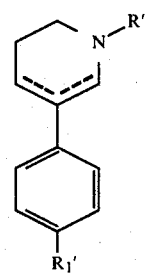

VIII wherein the dotted line indicates a mixture of 1,2,5,6 and 1,4,5,6 tetrahydropyridine isomers, submitting the mixture to catalytic hydrogenation to obtain a compound of the formula

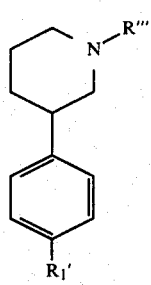

IX wherein R''' is R other than benzyl and when R''' is not hydrogen, submitting the latter to nitration to obtain a compound of the formula

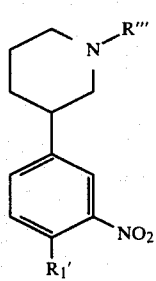

X which is reduced to form a compound of formula II' wherein R' is other than benzyl or when R''' is hydrogen, the compound of formula IX is reacted with an amine blocking agent to obtain a compound of the formula

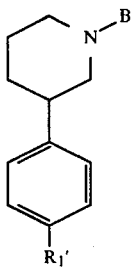

and reacting the latter in the same manner as the compound of formula IX to obtain the compound of formula II.

The formation of the magnesium derivative of the compound of formula V is preferably effected by reacting magnesium with the product of formula V, preferably in tetrahydrofuran, in the presence of a small amount of dibromethane as catalyst. The reaction of the magnesium derivative with the piperidone derivative of formula VI is preferably effected at low temperature at about 0° C. in tetrahydrofuran. The dehydration of the product of formula VII is preferably carried out at reflux in benzene in the presence of p-toluene sulfonic acid. Thionyl chloride or phosphoric anhydride or a mineral acid such as hydrochloric acid at reflux can also be used.

The catalytic hydrogenation of the product of formula VIII is preferably carried out in the presence of palladium. The nitration of the product of formula IX or IX' is preferably carried out with a trifluoroacetic acid - fuming nitric acid mixture and the fuming nitric acid can also be reacted in sulfuric acid or acetic anhydride.

The agent capable of blocking the amine of formula IX in a reversible manner is trifluoroacetic anhydride, preferably in the presence of a base when B is trifluoroacetyl or benzyl halide, and preferably benzyl bromide or chloride in the presence of a base when B is benzyl. The reduction of the nitro is preferably carried out by catalytic reduction generally with stannous chloride or ferrous chloride or copper acetylacetonate in the presence of sodium borohydride.

The compounds of formula I present a basic character and the acid addition salts of the compounds of formula I can advantageously be prepared by reacting a mineral or organic acid with the compound of formula I in substantially stoichiometric proportions. The salts can be prepared without isolating the corresponding bases.

The novel compositions having peripheral cardiovascular effects free of central effects are comprised of a pheripheral cardiovascularly effective amount of at least one compound of formula I and their non-toxic, pharmaceutically acceptable acid addition salts and an inert pharmaceutical carrier or excipient. The compositions may be in the form of tablets, dragees, capsules, granules, suppositories and injectable solutions or suspensions.

Examples of suitable excipients are talc, gum arabic, lactose, starch, magnesium stearate, cocoa butter, aqueous or nonaqueous vehicles, fatty substances of animal or vegetable origin, paraffin derivatives, glycols, various wetting agents, dispersants and emulsifiers and preservatives.

The compositions are endowed with remarkable dopaminergic properties causing peripheral cardio-vascular effects or peripheral vasodilatory properties, positively inotropic, and with very few central effects. They have a remarkable affinity for the post-synaptic dopaminergic receptors very dissociated from affinity for the α-adrenergic receptors. The compositions are useful for example, in the treatment of cerebral vascular accidents, peripheral circulatory disorders such as retinal or nephritic disorders or arteriopathy of the lower limbs and they can also be used in the treatment of cardiac insufficiencies of various etiologies.

The preferred compositions of the invention are those of formula I wherein R is hydrogen or alkyl of 1 to 5 carbon atoms and those wherein $R_1$ is —OH and their non-toxic, pharmaceutically acceptable acid addition salts. Particularly preferred is 1,3-dihydro-7-hydroxy-4-(3-piperidinyl)-2H-indol-2-one and its salts of addition with pharmaceutically acceptable acids.

The novel method of inducing peripheral cardio-vascular effects in warm-blooded animals, including humans, comprises administering to warm-blooded animals a peripheral vasodilatory effective amount of at least one compound of formula I and its non-toxic, pharmaceutically acceptable acid addition salts. The said compounds may be administered orally, rectally or parenterally and the usual daily dose is 0.07 to 2.75 mg/kg depending on the specific compound, the method of administration and the conditions treated. For example, the compound of Example 3 may be orally administered daily at 0.15 to 3 mg/kg for cardiac insufficiencies.

The novel intermediates of the invention are the compounds of the formulae

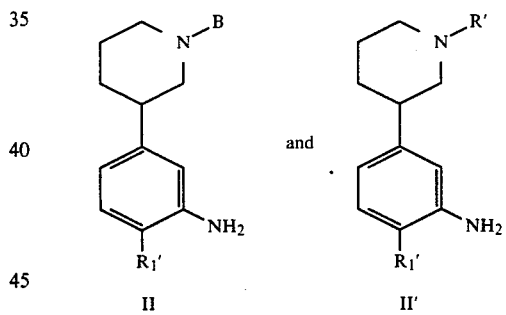

wherein B, R' and $R_1'$ have the above definitions and their haloamines.

In the following examples there are described several preferred embodiments to illustrate the invention. However, it should be understood that the invention is not intended to be limited to the specific embodiments.

EXAMPLE 1

1,3-dihydro-7-methoxy-4-(3-piperidinyl)-2H-indol-2-one

STEP A: 3-(4-methoxyphenyl)-1-benzyl-3-piperidinol 1 iodine crystal was sublimed by heating and was added to 5.25 g of magnesium turnings. After cooling, 10 ml of tetrahydrofuran, 1 ml of p-bromoanisole and 0.3 ml of dibromoethane were added thereto and the reaction was started by heating. Then, a mixture of 25 ml of p-bromoanisole and 120 ml of tetrahydrofuran was added dropwise and the mixture was heated for a further hour at reflux and left to stand for 16 hours to obtain a solution of a magnesium derivative. 100 ml of the said solution were cooled in an ice bath while a solution of 22 g of N-benzyl-3-piperidone in 100 ml of tetrahydrofuran was added dropwise with stirring under inert atmosphere over 80 minutes. The temperature was allowed to return to ambient, and the mixture was stirred for 2 hours. The mixture was cooled and 150 ml of saturated aqueous ammonium chloride solution were added dropwise. After extracting with ethyl acetate, washing several times with a 2 N aqueous solution of hydrochloric acid, making alkaline with addition of sodium hydroxide, extracting with methylene chloride, washing with water, drying and evaporating to dryness under reduced pressure, the oil obtained was chromatographed over silica and eluted with benzene - ethyl acetate 1-1 to obtain 23 g of 3-(4-methoxyphenyl)-1-benzyl-3-piperidinol melting at ≃58° C.

STEP B: Mixture of 3-(4-methoxyphenyl)-1-benzyl-1,2,5,6-tetrahydro and 3-(4-methoxyphenyl)-1-benzyl-1,4,5,6-tetrahydropyridine 7 g of the product of Step A, 10.15 g of p-toluene sulfonic acid and 300 ml of benzene were refluxed for 2 hours with with stirring under an inert atmosphere. After cooling, washing with 2 N sodium hydroxide, drying, evaporating to dryness under reduced pressure, purifying by chromatography over silica (eluent benzene - ethyl acetate 1-1), 5.6 g of mixture of 3-(4-methoxyphenyl)-1-benzyl-1,2,5, 6-tetrahydro and 3-(4-methoxyphenyl)-1-benzyl-1,4,5,6-tetrahydropyridine were obtained which was 1 g of 1,4,5,6-tetrahydropyridine isomer melting at 74° C. and 4.6 g of 1,2,5,6-tetrahydropyridine isomer melting at ≃98° C.

STEP C: 3-(4-methoxyphenyl)-1-(trifluoroacetyl)-piperidine

A solution of 15.5 g of the mixture of Step B in 250 ml of acetic acid absorbed 2.5 liters of hydrogen in the presence of 3.6 g of 10% palladium. After filtering, washing with acetic acid, evaporating to dryness under reduced pressure, adding 100 ml of water, cooling with an ice bath, alkalizing with ammonia, extracting with methylene chloride, drying, and evaporating to dryness under reduced pressure, 10.5 g of oil were obtained. A solution of the oil above in 60 ml of methylene chloride was cooled to 0° C. and 15.6 ml of trifluoroacetic anhydride were added dropwise. The mixture was stirred for 1 hour at ambient temperature and was evaporated to dryness under reduced pressure to eliminate the excess anhydride. The residue was taken up in methylene chloride and the solution was washed with a saturated solution of sodium bicarbonate, dried, evaporated to dryness under reduced pressure. Several ml of petroleum ether were added and the mixture was filtered to obtain 14.3 g of 3-(4-methoxyphenyl)-1-(trifluoroacetyl)-piperidine melting at 88° C.

STEP D: 3-(4-methoxy-3-nitrophenyl)-1-(trifluoroacetyl)-piperidine 2.24 ml of fuming nitric acid were added dropwise with stirring to 14.3 g of the product of Step C in 50 ml of trifluoroacetic acid at 0° C. The temperature was allowed to return to ambient and the mixture was stirred for 1 hour. After pouring the mixture on ice, extracting with methylene chloride, washing with water, drying, evaporating to dryness under reduced pressure, and purifying by chromatography over silica (eluent benzene - ethyl acetate 9-1), 12.3 g of 3-(4-methoxy-3-nitrophenyl)-1-(trifluoroacetyl)-piperidine were obtained which after crystallization from isopropyl ether melted at 96° C.

STEP E: 3-(3-amino-4-methoxyphenyl)-1-(trifluoroacetyl)-piperidine

A solution of 12.3 g of the product of Step D in 400 ml of ethanol absorbed 2.4 liters of hydrogen in the presence of 3.7 g of 10% palladium and after filtering, washing with ethanol, evaporating to dryness under reduced pressure, triturating the solid residue in isopropyl ethyl, filtering and drying, 9.4 g of 3-(3-amino-4-methoxyphenyl)-1-(trifluoroacetyl)-piperidine melting at 88° C. were obtained.

STEP F: 1,3-dihydro-7-methoxy-3-methylthio-4-[1-trifluoroacetyl)-3-piperidinyl]-2H-indol-2-one 604 mg of 3-(3-amino-4-methoxyphenyl)-1-trifluoroacetyl piperidine were added with stirring under an inert atmosphere to 20 ml of methylene chloride and 0.26 ml of ethyl methylthioacetate cooled to −65° C., and then 0.24 ml of tert-butyl hypochlorite were added over 5 minutes. After stirring for an hour, 0.29 ml of triethylamine were added dropwise and the temperature was allowed to return to ambient. 5 ml of aqueous 2 N hydrochloric acid were added and the mixture was stirred for an hour. The decanted organic phases were washed with water, dried and filtered. The filtrate was evaporated to dryness under reduced pressure and the residue was chromatographed over silica (eluent benzene-ethyl acetate 7-3) to obtain 580 mg of 1,3-dihydro-7-methoxy-3-methylthio-4-[1-trifluoroacetyl)-3-piperidinyl]-2H-indol-2-one which after crystallization from ethanol melted at ≃189° C.

STEP G: 1,3-dihydro-7-methoxy-4-[1-(trifluoroacetyl)-3-piperidinyl]-2H-indol-2-one 70 g of Raney's nickel were added with stirring under an inert atmosphere to a solution of 7.7 g of the product of Step F in 200 ml of tetrahydrofuran while maintaining the temperature at about 20° C. and the mixture was stirred for an hour. After filtering, rinsing with tetrahydrofuran, evaporating to dryness under reduced pressure, taking up the residue in methylene chloride, washing with water, drying, and evaporating to dryness under reduced pressure, 6.6 g of 1,3-dihydro-7-methoxy-4-[1-(trifluoroacetyl)-3-piperidinyl-2H-indol-2-one were obtained which after crystallization from ethanol melted at 174° C.

STEP H: 1,3-dihydro-7-methoxy-4-(3-piperidinyl)-2H-indol-2-one 6 g of the product of Step G in 150 ml of methanol and 60 ml of 2 N sodium hydroxide were stirred for an hour under an inert atmosphere. After extracting with methylene chloride, washing with water, drying, filtering, and evaporating to dryness under reduced pressure, 4.3 g of 1,3-dihydro-7-methoxy-4-(3-piperidinyl)-2H-indol-2-one were obtained which after crystallization from ethanol melted at 100° C. and then 168° C.

| Analysis | $C_{14}H_{18}N_2O_2$; molecular weight = 246.30 | | |
|---|---|---|---|
| Calculated | % C 68.26 | % H 7.36 | % N 11.38 |
| Found | 68.2 | 7.4 | 11.1 |

EXAMPLE 2

1,3-dihydro-7-methoxy-4-(1-propyl-3-piperidinyl)-2H-indol-2-one

A mixture of 2 g of the product of Example 1 in 40 ml of dimethylformamide, 3.39 g of potassium carbonate and 1.6 ml of propyl iodide was stirred under inert atmosphere for 90 minutes. After adding water, extracting with methylene chloride, washing with water, drying, evaporating to dryness under reduced pressure and purifying the residue by chromatography over silica (eluent: methylene chloride - methanol 9-1), 1.6 g of 1,3-dihydro-7-methoxy-4-(1-propyl-3-piperidinyl)-2H-indol-2-one melting at ≃120° C. were obtained.

| Analysis | $C_{17}H_{24}N_2O_2$; molecular weight = 288.38 | | |
|---|---|---|---|
| Calculated | % C 70.20 | % H 8.39 | % N 9.71 |
| Found | 70.5 | 8.5 | 9.6 |

EXAMPLE 3

1,3-dihydro-7-hydroxy-4-(3-piperidinyl)-2H-indol-2-one hydrobromide

A mixture of 1.5 g of the product of Example 1 in 15 ml of concentrated hydrobromic acid (d=1.49) was refluxed for 2 hours 30 minutes under an inert atmosphere and after evaporating to dryness under reduced pressure, taking up the residue with benzene, concentrating to dryness, adding 2 ml of ethanol, filtering the crystals obtained, drying under reduced pressure, and purifying by crystallization from ethanol, 1.4 g of 1,3-dihydro-7-hydroxy-4-(3-piperidinyl)-2H-indol-2-one hydrobromide melting at 190° C., then 250° C. were obtained.

| Analysis | $C_{13}H_{16}N_2O_2HBr$; molecular weight = 313.21 | | | |
|---|---|---|---|---|
| Calculated | % C 49.85 | % H 5.47 | % N 8.94 | % BR 25.52 |
| Found | 49.7 | 5.7 | 8.8 | 25.3 |

EXAMPLE 4

1,3-dihydro-7-hydroxy-4-(1-propyl-3-piperidinyl)-2H-indol-2-one hydrobromide 1.55 g of the product of Example 2 in 15 ml of 48% hydrobromic acid were refluxed for 2 hours with stirring under an inert atmosphere. After evaporating to dryness under reduced pressure, crystallizing the oil obtained from ethanol, filtering, washing with ether, drying, and purifying by crystallization from methanol, 1.31 g of 1,3-dihydro-7-hydroxy-4-(1-propyl-3-piperidinyl)-2H-indol-2-one hydrobromide melting at 210° C. were obtained.

| Analysis | $C_{16}H_{22}N_2O_2HBr$; molecular weight = 355.29 | | | |
|---|---|---|---|---|
| Calculated | % C 54.08 | % H 6.53 | % N 7.89 | % BR 22.49 |
| Found | 53.9 | 6.7 | 7.7 | 22.3 |

EXAMPLE 5

1,3-dihydro-7-methoxy-4-(1-methyl-3-piperidinyl)-2H-indol-2-one and its hydrochloride 4.5 g of the product of Example 1 were dissolved in 100 ml of methanol with stirring under an inert atmosphere and after cooling to about 5° C., 3.4 ml of 40% formic aldehyde were added dropwise. After stirring for 1 hour, 1.8 g of 95% sodium borohydride were added in small fractions and the mixture was stirred for 1 hour. The temperature was allowed to return to ambient and after diluting with iced water, extracting with methylene chloride, drying and evaporating to dryness under reduced pressure, filtering, washing with ether and drying, 4 g of 1,3-dihydro-7-methoxy-4-(1-methyl-3-piperidinyl)-2H-indol-2-one were obtained in the form of a base melting at ≃170° C.

1.6 g of the base were dissolved with warming in 30 ml of methanol and 5 ml of hydrogen chloride in methanol were added. 15 ml of the methanol were evaporated and after stirring to crystallize slowly by cooling in an ice bath, the crystals obtained were recovered by filtration and were washed with ether, dried at 80° C. under reduced pressure to obtain 1.44 g of 1,3-dihydro-7-methoxy-4-(1-methyl-3-piperidinyl)-2H-indol-2-one hydrochloride melting at >250° C.

| Analysis | $C_{15}H_{20}N_2O_2,HCl$; molecular weight = 296.80 | | | |
|---|---|---|---|---|
| Calculated | % C 60.70 | % H 7.13 | % N 9.44 | % Cl 11.94 |
| Found | 60.7 | 7.2 | 9.3 | 11.8 |

EXAMPLE 6

1,3-dihydro-7-hydroxy-4-(1-methyl-3-piperidinyl)-2H-indol-2-one hydrobromide

A mixture of 2.2 g of the product of Example 5 in 25 ml of 48% hydrobromic acid was refluxed for 3 hours with stirring under an inert atmosphere. After evaporating to dryness under reduced pressure, taking up the residue in ethanol, filtering the crystallized product, washing with acetone and drying under reduced pressure, 2.5 g of 1,3-dihydro-7-hydroxy-4-(1-methyl-3-piperidinyl)-2H-indol-2-one hydrobromide were obtained which after crystallization from methanol melted at >250° C.

| Analysis | $C_{14}H_{18}N_2O_2$; molecular weight = 327.23 | | | |
|---|---|---|---|---|
| Calculated | % C 51.38 | % H 5.85 | % N 8.58 | % BR 24.42 |
| Found | 51.2 | 5.8 | 8.6 | 24.2 |

EXAMPLE 7

Tablets were prepared containing 5 mg of 1,3-dihydro-7-hydroxy-4-(3-piperidinyl)-2H-indol-2-one hydrobromide or 10 mg of 1,3-dihydro-7-hydroxy-4-(1-propyl-3-pyridinyl)-2H-indol-2-one hydrobromide and sufficient excipient of lactose, starch, talc and magnesium stearate for a tablet of 100 mg.

PHARMACOLOGICAL DATA

A. Rotation behavior after unilateral lesion of the nigra-striated bundle by 6-hydroxydopamine Male rats weighing about 220 g were injured in the nigra-striated dopaminergic bundle by Ungerstedt's method [Acta physiol. Scand. 1971, Vol. 82 suppl. p. 367–69 93] modified by unilateral injection of 9.2 µg of 6-hydroxydopamine hydrochloride in solution in 4 µl of physiological solution containing 0.5 mg/ml of ascorbic acid. The test products were administered intraperitoneally and the animals treated, on average 6, were placed individually in a rotometer which enabled the counting of the number of rotations carried out by each animal in the opposite direction to the injured side. East test was continued for at least ninety minutes under the conditions of the experiment, the following results were obtained: The product of Example 3 caused practically no rotations at a dose of 5 mg/kg and was therefore substantially deprived of dopaminergic stimulating activity at the central level.

B. Stereotype Beavior

The tests were carried out on groups of 5 male rats weighing 150 to 180 g and each animal was placed individually in a barred cage (29×25×17 cm) containing a few wood shavings. The test product was administered intraperitoneally and the behavior of the animals was noted every half-hour for 5 hours with the rating of Halliwell et al [Brit. J. Pharmacol. 1964, Vol. 23, 330–350]. The animal was asleep (0), it was awake but immobile (1), it turned in the cage (2), it sniffed the cover (3), it licks the walls (4), it touched the wood shavings or the bars of the cage with its teeth (5), it bit the shavings or the bars of the cage (6). The total was determined of the scores per group taken at different times after administration of the product studied and at a dose of 50 mg/kg, the product of Example 3 caused practically no stereotype movements and was therefore substantially deprived of dopaminergic agonist action at the central level.

C. Hypotensive Activity

The hypotensive activity was studied on male rats of the WISTAR strain weighing about 300 g and anesthetized with nembutal (50 mg/kg by intraperitoneal route). The product tested was administered intravenously into the jugular vein and the carotidien arterial pressure was measured before and after administration of the product tested. At a dose of 1 mg/kg, the product of Example 3 had a slight effect on the arterial pressure.

D. Test for Direct Vasodilatary Activity of Vascular Relaxing Postsynaptic-activity Rats of the Sprague-Dawley strain weighing 320–350 g were anesthetized with pentobarbital (50 mg/kg by intraperitoneal injection) and after the positioning of a carotidien catheter to measure the arterial pressure and a jugular catheter for the injection of the test compounds and possible antagonists, the animals were demedullated with a steel rod. This rod was introduced by the right orbital orifice and descended the length of the spinal cord. The animals were then immediately placed under assisted respiration and a few minutes after the arterial pressure was stabilized, the animals received an intravenous perfusion of angiotensine II of 50 g/kg/min to increase their average pressure by about 100 mm of mercury. After a plateau was reached, the test substance was injected intravenously every 2 minutes and in cumulated doses. The percentage drop in the average arterial pressure obtained enabled a dose-response curve to be traced reflecting the vasodilatary activity of the compound studied. The preliminary treatment of the animals with different antagonists enabled the mechanism of action of the compound to be determined. The products were tested between 0.001 and 1 mg/kg and Domperidone and propanolol were used as antagonists. The product of Example 3 had a dose dependent vasodilator effect from 0.001 mg/kg and this effect was of dopaminergic and α-adrenergic origin.

E. Positive inotropic activity

Rats of Sprague-Dawley strain weighing 300 to 350 g were anesthetized with pentobarbital (50 mg/kg by intraperitoneal injection) and a catheter was placed in the left ventricle to measure the cardiac intraventricular pressure and the dP/dt VG (or rate of variation of the intraventricular pressure). A second arterial catheter placed in the femoral artery enabled the systemic arterial pressure and the cardiac frequency to be registered. The test products and the possible antagonists were injected by a catheter placed in a jugular vein. This model enabled the effect of various substances on the force of cardiac contraction to be evaluated in vivo as a function of the dose and the time. The substances which possess a positive inotropic effect increase the dP/dt, the maximal ventricular pressure and the differential pressure. The product of Example 3 administered at a dose of 10 to 100 mg/kg caused an increase of the dP/dt and of the maximal ventricular pressure which was not otherwise blocked by propanolol. The product of Example 3 therefore possessed positive inotropic properties.

F. Presynaptic activity at the vascular level

Rats of Sprague-Dawley strain weighing 320–350 g were anesthetized with pentobarbital (50 mg/kg by intraperitoneal injection) and after insertion of a carotidien catheter to measure the arterial pressure and a jugular catheter for the injection of the test compounds, the animals were demedullated with a stainless steel rod introduced by the right orbitary orifice. This rod was insulated along its length with the exception of the last five centimeters. As soon as the medulla was destroyed, the animals were placed under assisted respiration. After a period of rest of about 20 minutes, the animals were submitted to electrical stimulations applied between the demedullation rod and a neutral electrode placed under the skin in the thigh region with impulses of 2 msec., frequency of 10 Hz and amplitude of about 20 V for 30 sec. for 5 minutes each. After stabilizing the responses, the test compounds were administered intravenously and the alteration of the amplitude of the pressure responses to the electrical stimulation resulted in a presynaptic action (a reduction in the response indicating a reduction in the liberation of noradrenaline) or a direct or postsynaptic vascular action (α-blocker effect, directly vasodilatory). The addition of appropriate blockers and the combination of this technique with the modification of dose-response curves to vasoconstricting agents such as noradrenaline enabled the pharmacological profile of the test compound to be determined. The product of Example 3 caused a reduction of the responses which was not blocked by sulpiride. This reduction of the responses is linked to an essentially post-synaptic activity.

G. Acute toxicity

The lethal doses $LD_{50}$ of the different compounds tested were evaluated after oral administration to mice and $LD_0$ is the maximum dose not causing any mortality in 8 days.

The following results were obtained.

| Products of Example | $LD_0$ in mg/kg |
| --- | --- |
|  | 0 |
|  | 0 |
| 3 | 400 |
| 4 | 400 |

Various modifications of the products and method of the invention may be made without departing from the spirit or scope thereof and it is to be understood that the invention is intended to be limited only as defined in the appended claims.

What is claimed is:

1. A compound selected from the group consisting of 7-hydroxy-indoles of the formula

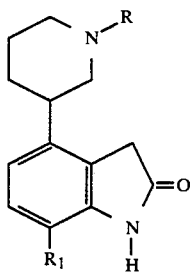

wherein R is selected from the group consisting of hydrogen, alkyl of 1 to 5 carbon atoms, cycloalkylalkyl of 4 to 7 carbon atoms and aralkyl of 7 to 12 carbon atoms optionally substituted by one or more members of the group consisting of alkyl and alkoxy of 1 to 5 carbon atoms, halogen and alkenyl and alkynyl of 3 to 5 carbon atoms with the multiple bond being other than between the carbons α- and β- to the nitrogen atom, $R_1$ is selected from the group consisting of —OH, alkoxy of 1 to 5 carbon atoms, phenoxy and phenylalkoxy of 7 to 9 carbon atoms and their non-toxic, pharmaceutically acceptable acid addition salts.

2. A compound of claim 1 wherein $R_1$ is —OH.

3. A compound of claim 1 wherein R is hydrogen or alkyl of 1 to 5 carbon atoms.

4. A compound of claim 2 wherein R is hydrogen or alkyl of 1 to 5 carbon atoms.

5. A compound of claim 1 selected from the group consisting of 1,3-dihydro-7-hydroxy-4-(3-piperidinyl-2H-indol-2-one and its non-toxic, pharmaceutically acceptable acid addition salts.

6. A composition having peripheral cardiovascular activity comprising an amount of at least one compound of claim 1 sufficient to impart peripheral cardiovascular activity and an inert pharmaceutical carrier.

7. A composition of claim 6 wherein $R_1$ is —OH.

8. A composition of claim 6 wherein R is hydrogen or alkyl of 1 to 5 carbon atoms.

9. A composition of claim 7 wherein R is hydrogen or alkyl of 1 to 5 carbon atoms.

10. A composition of claim 6 wherein the active compound is selected from the group consisting of 1,3-dihydro-7-hydroxy-4-(3-piperidinyl)-2H-indol-2-one and its non-toxic, pharmaceutically acceptable acid addition salts.

11. A method of inducing peripheral cardiovascular effects in warm-blooded animals comprising administering to warm-blooded animals a peripheral vasodilatory effective amount of at least one compound of claim 1.

12. A method of claim 11 wherein $R_1$ is —OH.

13. A method of claim 11 wherein R is hydrogen or alkyl of 1 to 5 carbon atoms.

14. A method of claim 12 wherein R is hydrogen or alkyl of 1 to 5 carbon atoms.

15. A method of claim 11 wherein the active compound is selected from the group consisting of 1,3-dihydro-7-hydroxy-4-(3-piperidinyl)-2H-indol-2-one and its non-toxic, pharmaceutically acceptable acid addition salts.

* * * * *